US009579429B2

(12) United States Patent
Williams et al.

(10) Patent No.: US 9,579,429 B2
(45) Date of Patent: Feb. 28, 2017

(54) SURGICAL CASSETTE WITH COMPLIANT CLAMPING ZONE

(75) Inventors: David Williams, Newport Beach, CA (US); David Domash, Irvine, CA (US); Jeffrey Jikang Chun, Irvine, CA (US); Mark A. Hopkins, Mission Viejo, CA (US)

(73) Assignee: Novartis AG, Basel (CH)

( * ) Notice: Subject to any disclaimer, the term of this patent is extended or adjusted under 35 U.S.C. 154(b) by 2515 days.

(21) Appl. No.: 11/391,859

(22) Filed: Mar. 29, 2006

(65) Prior Publication Data
US 2007/0252395 A1    Nov. 1, 2007

(51) Int. Cl.
| B65D 45/00 | (2006.01) |
| A61M 1/00 | (2006.01) |
| A61B 17/00 | (2006.01) |
| A61F 9/007 | (2006.01) |

(52) U.S. Cl.
CPC ......... *A61M 1/0058* (2013.01); *A61F 9/00736* (2013.01); *A61M 2205/12* (2013.01); *Y10T 292/20* (2015.04)

(58) Field of Classification Search
CPC ........... A61F 9/000736; A61M 1/0058; A61M 2205/12; Y10T 292/20
USPC .................................. 606/1; 604/30, 34, 65
See application file for complete search history.

(56) References Cited

U.S. PATENT DOCUMENTS

| 3,756,752 A | 9/1973 | Stenner | |
| 4,081,686 A * | 3/1978 | Nieuweboer | 378/187 |
| 4,256,442 A | 3/1981 | Lamadrid et al. | |
| 4,395,258 A | 7/1983 | Wang et al. | |
| 4,493,695 A | 1/1985 | Cook | |
| 4,626,248 A | 12/1986 | Scheller | |

(Continued)

FOREIGN PATENT DOCUMENTS

| AU | 703803 | 7/1997 |
| EP | 0786260 B1 | 7/1997 |

(Continued)

OTHER PUBLICATIONS

EP Search Report, EP 07 10 9823, dated Sep. 6, 2007, Published Dec. 19, 2007, 2 Pages.

(Continued)

*Primary Examiner* — Gary Jackson
*Assistant Examiner* — Boniface N Nganga
(74) *Attorney, Agent, or Firm* — Darien Reddick

(57) ABSTRACT

Embodiments of the present invention provide a surgical cassette with compliant clamping zones to provide more uniform loading. According to one embodiment of the present invention, a surgical cassette includes a clamping portion that is configured to deform to conform to non-uniform load profile applied to the cassette. The clamping portion can include ribs that are sized and made of a suitable material such that the ribs will deflect predictably in the elastic region and flow plastically when the material yield point is exceeded. The use of ribs creates discrete small load areas that will deflect and distort predictably and non-catastrophically at high loads. This allows for the absorption of accumulated tolerances between the clamping mechanism and cassette (e.g., the non-parallelism between the clamping mechanism and cassette) while still providing a distributed load on the cassette.

15 Claims, 8 Drawing Sheets

(56) References Cited

U.S. PATENT DOCUMENTS

| | | | |
|---|---|---|---|
| 4,627,833 A | 12/1986 | Cook | |
| 4,650,469 A * | 3/1987 | Berg | A61M 5/142 |
| | | | 417/474 |
| 4,713,051 A | 12/1987 | Steppe | |
| 4,735,558 A | 4/1988 | Kienholz et al. | |
| 4,758,220 A | 7/1988 | Sundblom et al. | |
| 4,758,238 A | 7/1988 | Sundblom | |
| 4,790,816 A | 12/1988 | Sundblom | |
| 4,798,580 A | 1/1989 | DeMeo et al. | |
| 4,798,850 A | 1/1989 | Brown | |
| 4,824,339 A | 4/1989 | Bainbridge et al. | |
| 4,904,168 A | 2/1990 | Cavoto et al. | |
| 4,927,411 A | 5/1990 | Pastrone et al. | |
| 5,125,891 A | 6/1992 | Hossain et al. | |
| 5,195,960 A | 3/1993 | Hossain et al. | |
| 5,230,614 A | 7/1993 | Zanger et al. | |
| 5,267,956 A | 12/1993 | Beuchat et al. | |
| 5,281,400 A | 1/1994 | Berry, Jr. | |
| 5,324,180 A | 6/1994 | Zanger | |
| 5,330,331 A | 7/1994 | Doede | |
| 5,364,342 A | 11/1994 | Beuchat et al. | |
| 5,387,088 A | 2/1995 | Knapp et al. | |
| 5,397,222 A * | 3/1995 | Moss | A61M 5/1413 |
| | | | 417/477.2 |
| 5,417,395 A | 5/1995 | Fowler | |
| 5,445,506 A | 8/1995 | Afflerbaugh et al. | |
| 5,588,815 A | 12/1996 | Zaleski, II | |
| 5,676,530 A | 10/1997 | Nazarifar | |
| 5,746,708 A | 5/1998 | Giesler et al. | |
| 5,810,770 A | 9/1998 | Chin | |
| 6,036,458 A | 3/2000 | Cole | |
| 6,053,543 A | 4/2000 | Arabia et al. | |
| 6,059,544 A | 5/2000 | Jung | |
| 6,059,765 A | 5/2000 | Cole et al. | |
| 6,076,868 A | 6/2000 | Roger, Jr. et al. | |
| 6,101,406 A | 8/2000 | Hacker | |
| 6,267,956 B1 | 7/2001 | Gomes | |
| 6,272,833 B1 | 8/2001 | Stephan | |
| 6,293,926 B1 | 9/2001 | Sorenson | |
| 6,302,455 B1 | 10/2001 | Huang | |
| 6,342,061 B1 | 1/2002 | Kauker et al. | |
| 6,364,342 B1 | 4/2002 | Kim | |
| 6,572,349 B2 | 6/2003 | Sorensen et al. | |
| 7,070,578 B2 | 7/2006 | Leukanech et al. | |
| 7,712,802 B2 | 5/2010 | Williams et al. | |
| 2001/0016711 A1 | 8/2001 | Sorenson | |
| 2003/0190244 A1 * | 10/2003 | Davis et al. | 417/477.2 |
| 2003/0202894 A1 | 10/2003 | Leukanech | |
| 2003/0204172 A1 | 10/2003 | Steppe | |
| 2003/0225363 A1 | 12/2003 | Gordon | |
| 2004/0074281 A1 | 4/2004 | Lobdell | |
| 2004/0106915 A1 | 6/2004 | Thoe | |
| 2004/0149930 A1 * | 8/2004 | Ando | 250/484.4 |
| 2004/0253129 A1 | 12/2004 | Sorenson | |
| 2005/0065462 A1 | 3/2005 | Nazarifar | |
| 2005/0186098 A1 * | 8/2005 | Davis et al. | 417/477.2 |
| 2005/0234395 A1 | 10/2005 | Mackool | |
| 2005/0285025 A1 | 12/2005 | Boukhny et al. | |
| 2007/0286755 A1 | 12/2007 | Williams et al. | |
| 2008/0015515 A1 | 1/2008 | Hopkins et al. | |

FOREIGN PATENT DOCUMENTS

| | | |
|---|---|---|
| EP | 1366775 A1 | 3/2003 |
| EP | 1366776 A1 | 3/2003 |
| EP | 1356835 A1 | 10/2003 |
| EP | 1512421 | 3/2005 |
| EP | 1849488 A1 | 10/2007 |
| EP | 1867349 A1 | 12/2007 |
| EP | 1872810 A1 | 1/2008 |
| GB | 2051455 | 5/1979 |
| GB | 2080144 | 2/1982 |
| JP | 2003284769 | 10/2003 |
| JP | 2003-319964 | 11/2003 |
| JP | 2005-016057 | 1/2005 |
| WO | 2002024252 | 3/2002 |
| WO | 2004108189 | 12/2004 |

OTHER PUBLICATIONS

EP Search Report, EP 07 104 111, dated Sep. 5, 2007, Published Oct. 31, 2007, 2 Pages.

EP Search Report, EP 07 11 0589, dated Oct. 2, 2007, Published Jan. 2, 2008, 3 Pages.

* cited by examiner

US 9,579,429 B2

SURGICAL CASSETTE WITH COMPLIANT CLAMPING ZONE

TECHNICAL FIELD OF THE INVENTION

The present invention relates to surgical cassettes. More particularly, the present invention relates to surgical cassettes used in ophthalmic surgical systems. Even more particularly, the present invention relates to surgical cassettes with compliant clamping zones.

BACKGROUND OF THE INVENTION

The human eye can suffer a number of maladies causing mild deterioration to complete loss of vision. While contact lenses and eyeglasses can compensate for some ailments, ophthalmic surgery is required for others. Generally, ophthalmic surgery is classified into posterior segment procedures, such as vitreoretinal surgery, and anterior segment procedures, such as cataract surgery. More recently, combined anterior and posterior segment procedures have been developed.

The surgical instrumentation used for ophthalmic surgery can be specialized for anterior segment procedures or posterior segment procedures or support both. In any case, the surgical instrumentation often requires the use of associated consumables such as surgical cassettes, fluid bags, tubing, hand piece tips and other consumables.

A surgical cassette can provide a variety of functions depending on the procedure and surgical instrumentation. For example, surgical cassettes for cataract surgeries (e.g., phacoemulsification procedures) help manage irrigation and aspiration flows into and out of a surgical site. Surgical cassettes can also provide support for fluid bags, a manifold for directing vacuum/pressure to surgical instrumentation, and other functionality.

Cassettes are generally coupled to the surgical instrumentation at a cassette receiving site. When the cassette is inserted into the cassette receiver, a clamp closes on the cassette to hold the cassette in place. During operation, the surgical cassette can experience a significant amount of force in the clamping area. This force can be the result of the clamps counteracting a force applied by a peristaltic pump pushing near the center of the cassette or other forces.

Often the force in the clamping zone of a cassette is not evenly distributed. This can be the result of differences in dimensional tolerances between the clamp and the cassette or other factors that cause the clamp and cassette to be non-parallel. The uneven distribution of force can cause the clamping zone of the cassette to fail, potentially inflicting catastrophic damage on the cassette itself.

Therefore, a need exists for a surgical cassette that distributes uneven loading to prevent failure.

SUMMARY OF THE INVENTION

Embodiments of the present invention provide a surgical cassette with a clamping portion that distributes the load applied by a clamp. The clamping portion can comprise a set of ribs to distribute the load of the clamp. Each rib in the set of ribs can be formed of a material that deforms elastically in an elastic region and plastically when a material yield point is reached. Consequently, the clamping portion can, according to one embodiment, conform to the load profile put on it.

Another embodiment of the present invention can include a surgical cassette having a body portion to house at least a portion of a fluidics management system for an ophthalmic surgery process, a first clamping portion attached to (e.g., as part of a unitary piece or coupled to) the body portion and a second clamping portion attached to the body portion. The clamping portions can be located at the top, bottom or sides of the surgical cassette. The surgical cassette is adapted for insertion into a cassette receiver in a surgical console and the clamping portions are configured to deform to distribute the load asserted by a clamp holding the surgical cassette in place at the surgical console.

Embodiments of the present invention provide an advantage by helping provide uniform load distribution on a cassette.

Embodiments of the present invention provide another advantage by absorbing tolerance accumulations of the clamping mechanism and cassette, particularly the non-parallelism of the clamp and the cassette.

Embodiments of the present invention provide another advantage by helping to prevent blow out of elastomers on the cassette if a fluid passage on the cassette is over-pressurized. The compliant clamping zones reduce or eliminate the need for adhesive or any other bonding methods to ensure that the elastomers do not blow off.

BRIEF DESCRIPTION OF THE DRAWINGS

A more complete understanding of the present invention and the advantages thereof may be acquired by referring to the following description, taken in conjunction with the accompanying drawings in which like reference numbers indicate like features and wherein.

DETAILED DESCRIPTION OF THE INVENTION

Preferred embodiments of the invention are illustrated in the FIGURES, like numerals being used to refer to like and corresponding parts of the various drawings.

Embodiments of the present invention provide a surgical cassette with compliant clamping zones to provide more uniform loading. According to one embodiment of the present invention, a surgical cassette includes a clamping portion that is configured to deform in order to conform to a non-uniform load profile applied to the cassette. The clamping portion can include ribs that are sized and made of a suitable material such that the ribs will deflect predictably in the elastic region and flow plastically when the material yield point is exceeded. The use of ribs creates discrete small load areas that will deflect and distort predictably and non-catastrophically at high loads. This allows for the absorption of accumulated tolerances between the clamping mechanism and cassette (e.g., the non-parallelism between the clamping mechanism and cassette) while still providing a distributed load on the cassette.

Figure 1:
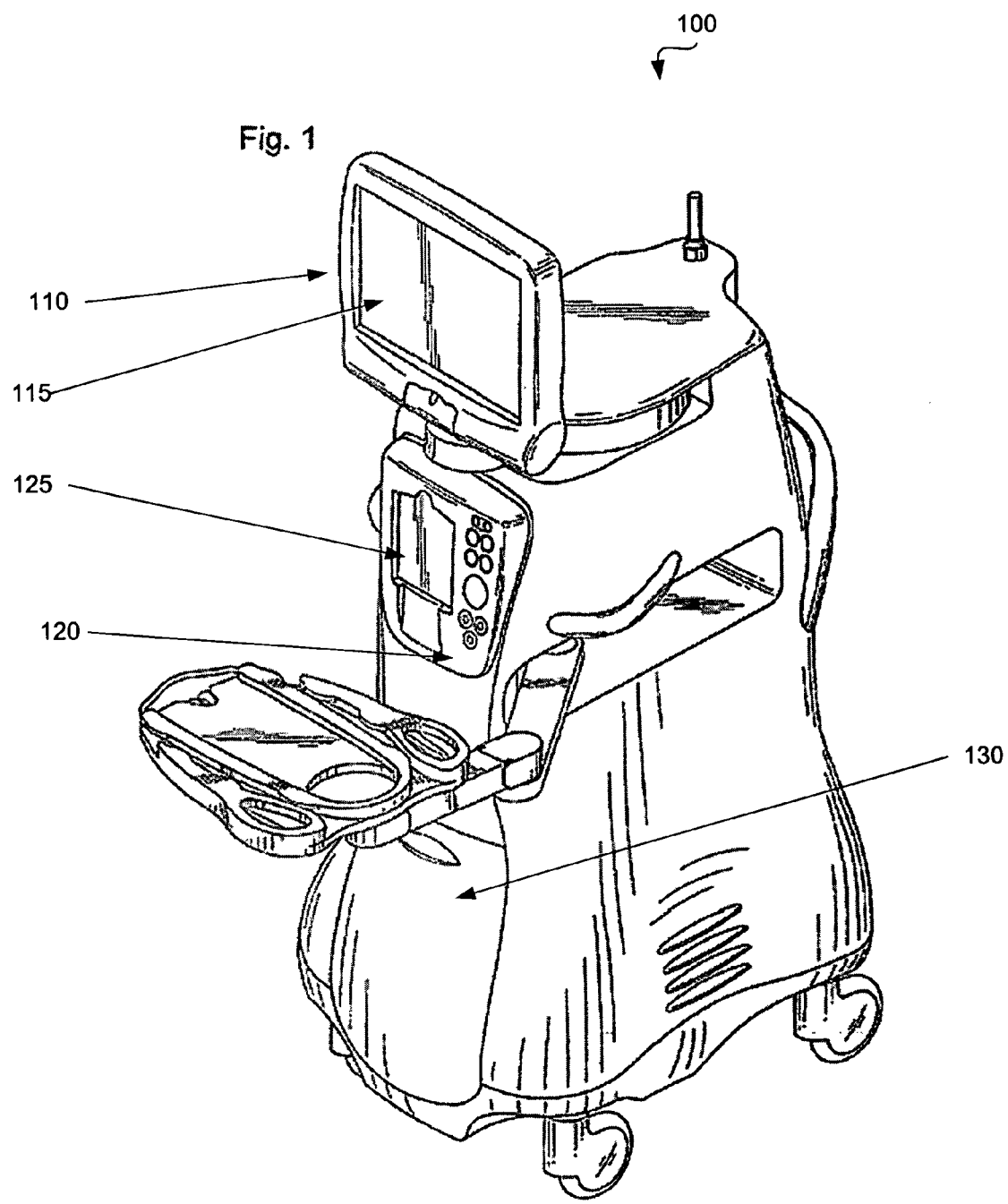
FIG. 1 is a diagrammatic representation of one embodiment of a surgical console.

FIG. 1 is a diagrammatic representation of one embodiment of an ophthalmic surgical console 100. Surgical console 100 can include a swivel monitor 110 that has touch screen 115. Swivel monitor 110 can be positioned in a variety of orientations for whomever needs to see touch screen 115. Swivel monitor 110 can swing from side to side, as well as rotate and tilt. Touch screen 115 provides a graphical user interface ("GUI") that allows a user to interact with console 100.

Surgical console 100 also includes a connection panel 120 used to connect various tools and consumables to surgical console 100. Connection panel 120 can include, for example, a coagulation connector, balanced salt solution receiver, connectors for various hand pieces and a fluid management system ("FMS") or cassette receiver 125. Surgical console 100 can also include a variety of user friendly features, such as a foot pedal control (e.g., stored behind panel 130) and other features.

In operation, a cassette (not shown) can be placed in cassette receiver 125. A clamp in surgical console 100 clamps the cassette in place to minimize movement of the cassette during use. The clamp can clamp the top and bottom of the cassette, the sides of the cassette or otherwise clamp the cassette.

Surgical console 100 is provided by way of example and embodiments of the present invention can be implemented with a variety of surgical systems. Example surgical systems in which cassettes according to various embodiments of the present invention can be used include, for example, the Series 2000® Legacy® cataract surgical system, the Accurus® 400VS surgical system, and the Infiniti™ Vision System surgical system, all available from Alcon Laboratories Inc. of Fort Worth, Tex. Additionally, embodiments of the present invention can be used with a variety of surgical cassettes, examples of which are described in U.S. Pub. Nos. 2005/0186098 (application Ser. No. 11/114,289 to Davis et al.), 2004/0253129 (application Ser. No. 10/891,642 to Sorensen et al.), 2005/0065462 (application Ser. No. 10/979,433 to Nazarifar et al.), 2003/0225363 (application Ser. No. 10/156,175 to Gordon et al.), 2001/0016711 (application Ser. No. 09/846,724 to Sorensen et al.) and U.S. Pat. No. 6,293,926 to Sorensen et al., U.S. Pat. No. 4,493,695 to Cook, U.S. Pat. No. 4,627,833 to Cook, U.S. Pat. No. 4,395,258 to Wang et al, U.S. Pat. No. 4,713,051 to Steppe, et al., U.S. Pat. No. 4,798,850 to DeMeo, et al., U.S. Pat. No. 4,758,238 to Sundblom et al, U.S. Pat. No. 4,790,816 to Sundblom et al., U.S. Pat. No. 6,267,956 to Beuchat, U.S. Pat. No. 6,364,342 to Beuchat, U.S. Pat. No. 6,036,458 to Cole et al and U.S. Pat. No. 6,059,544 to Jung et al., each of which is hereby fully incorporated by reference herein. Embodiments of the present invention can be implemented for other suitable surgical systems and cassettes as would be understood by one of ordinary skill in the art.

Figure 2:
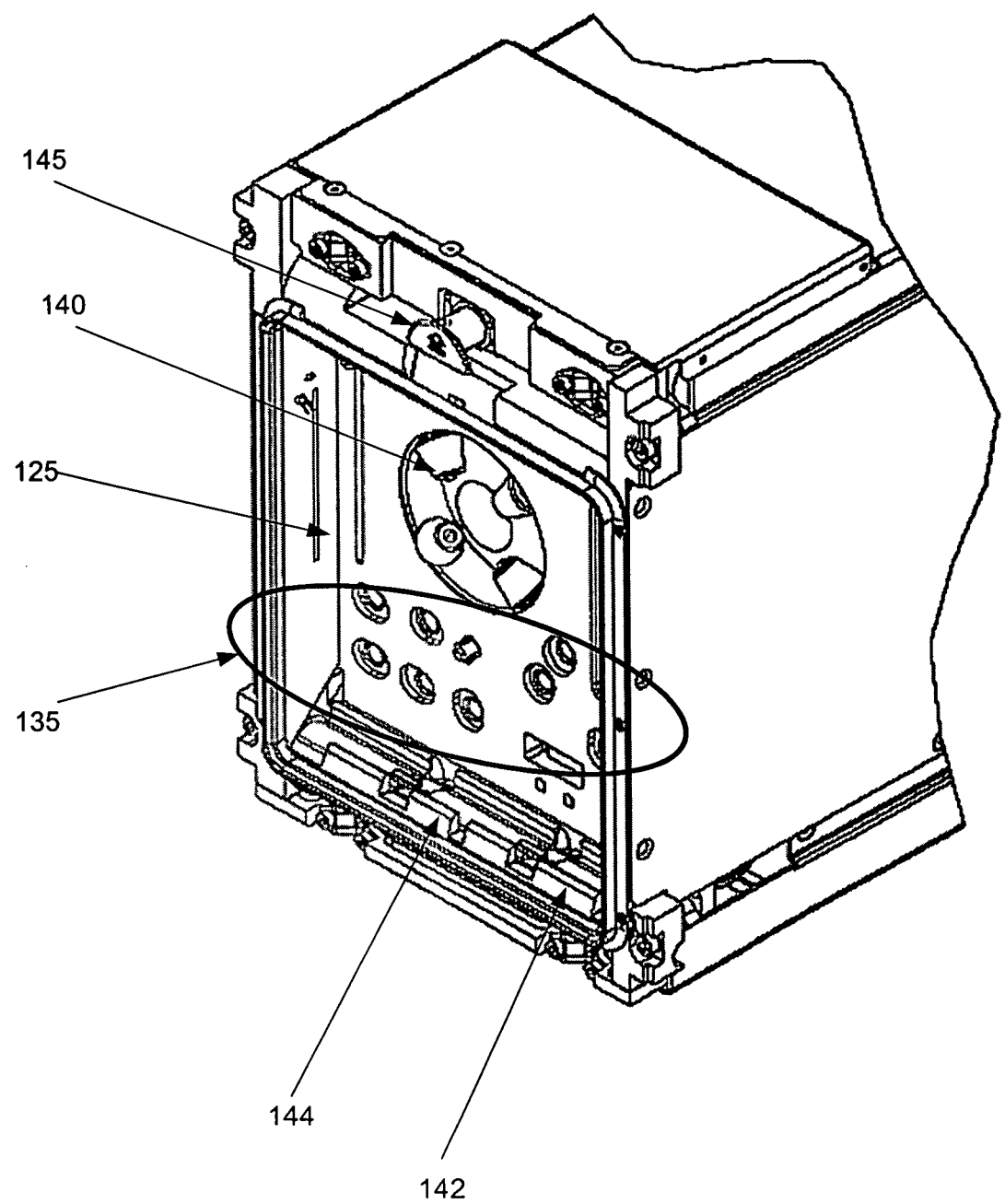
FIG. 2 is a diagrammatic representation of one embodiment of a cassette receiver.

FIG. 2 is a diagrammatic representation of one embodiment of cassette receiver 125 without a cassette. Cassette receiver 125 can have various input and output ports (indicated generally at 135) to receive fluids (i.e., liquids and gasses) from the surgical cassette. Cassette receiver 125 can further include an opening to allow peristaltic pump rollers 140 to contact the surgical cassette during operation. One embodiment of a peristaltic pump and complimentary cassette is described in U.S. Pat. No. 6,293,926 to Sorensen, which is hereby fully incorporated by reference herein.

The surgical cassette, in the embodiment of FIG. 2, is held in place by a clamp having a bottom rail 142 and a top rail (not shown). Each rail can have clamping fingers (e.g., clamp finger 144) that contact the cassette in corresponding clamping zones. One embodiment of a surgical cassette clamp is described in United States Patent Pub. No. 2003/0202894 (application Ser. No. 10/132,797 to Leukanech), which is hereby fully incorporated by reference herein. A release button 145 is pressed to initiate release of the cassette from the clamp. Depending on the surgical console 100, the cassette release process can include several steps, including venting of pressure or fluids, disengaging the clamps or other steps. The configuration of FIG. 2 is provided by way of example. The form factor of cassette receiver 125, placement and number of input/output ports and other features of cassette receiver 125 can depend on the surgical console 100, surgical procedure being performed or other factors.

Figure 3:
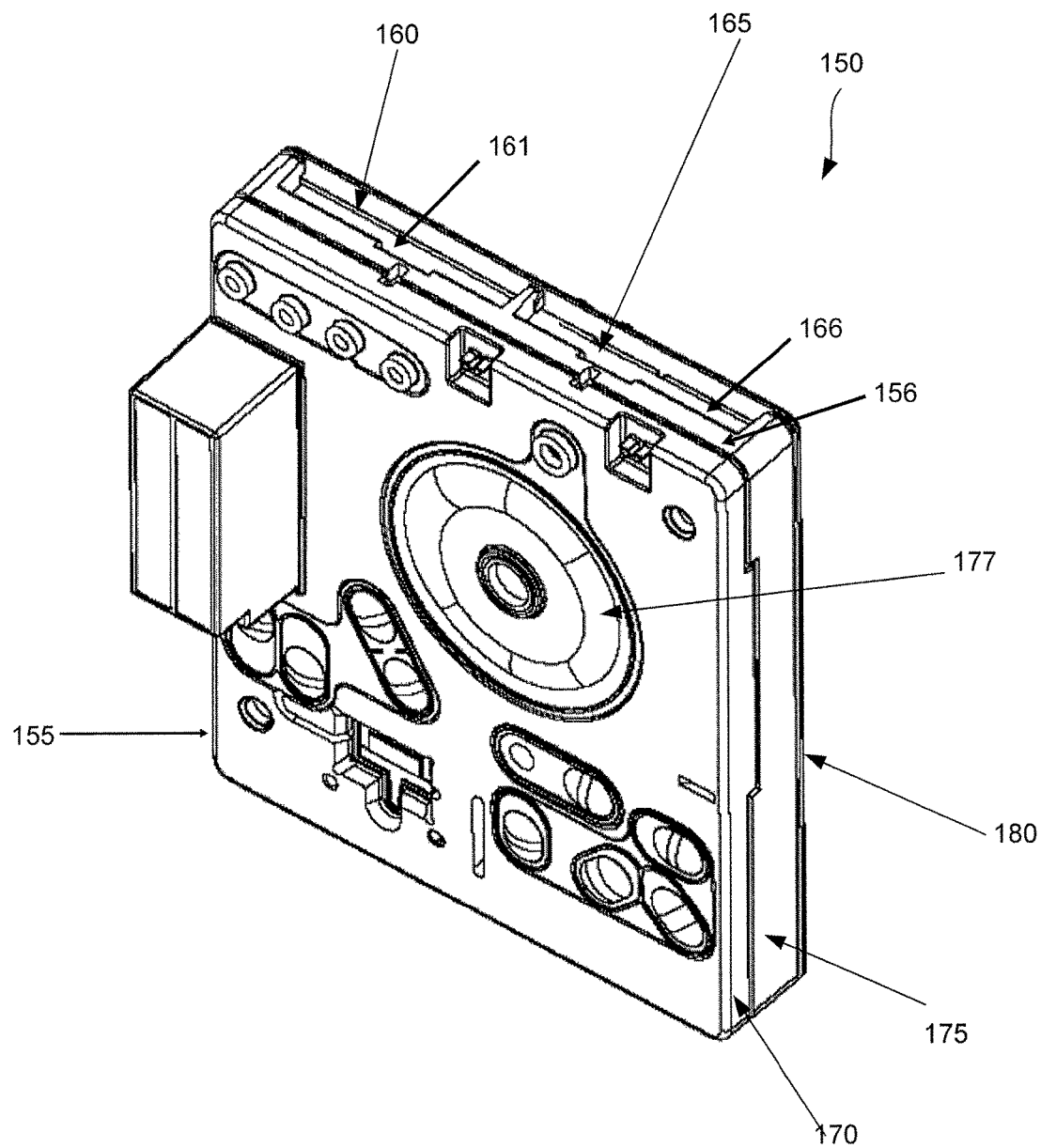
FIG. 3 is a diagrammatic representation of one embodiment of a surgical cassette.

FIG. 3 is a diagrammatic representation of one embodiment of a surgical cassette 150. Cassette 150 can provide a closed system fluidic device that can be discarded following a surgical procedure. Cassette 150 can include a cassette body 155 having an outer peripheral wall 156 and portions that interface with the clamp (e.g., indicated generally at clamping zones 160 and 165) projecting from the cassette body 155. In the embodiment shown, cassette 150 is formed from three primary sections: an inner or surgical console interface section 170 that faces the surgical console when cassette 150 is inserted into surgical console 100, a middle section 175 and a back plate 180. The various sections of cassette 150 can be coupled together via a press fit, interlocking tabs, chemical bonding, thermal bonding, mechanical fasteners or other attachment mechanism known in the art. In other embodiments, cassette 150 can be formed of a single piece or multiple pieces.

Surgical console interface section 170 can provide an interface for fluid flow channels (e.g., flow channel 177 for the peristaltic pump provided by an elastomeric pump membrane), valves (e.g., irrigation/aspiration valves), pressure sensors and other features to manage fluid flow. Cassette 150 can also attach to a fluid bag (not shown) to collect fluids during a procedure.

In operation, cassette 150 is held in place in cassette receiver 125 by clamp rails that contact cassette 150 in the clamping zones. For example, the upper clamp rail will contact cassette 150 in clamping zone 160 and clamping zone 165 while the bottom clamp rail (e.g., bottom clamp rail 142) will contact cassette 150 at similar bottom clamping zones.

Figure 4:
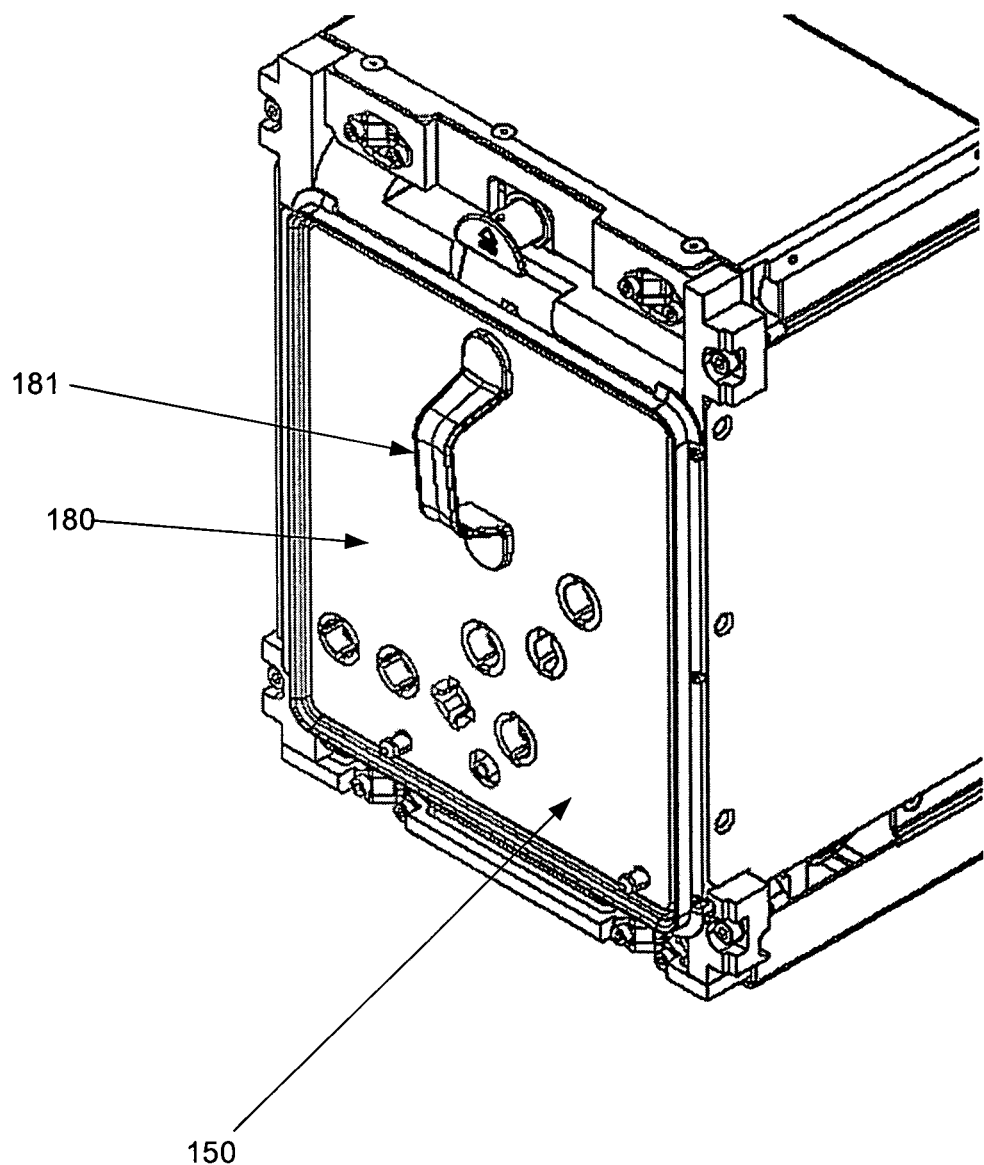
FIG. 4 is a diagrammatic representation of one embodiment of a surgical cassette in a cassette receiver.

FIG. 4 is a diagrammatic representation of cassette 150 inserted in cassette receiver 125. As can be noted from FIG. 4, back plate 180 can include a handle 181 for one-handed insertion and removal of cassette 150.

Figure 5:
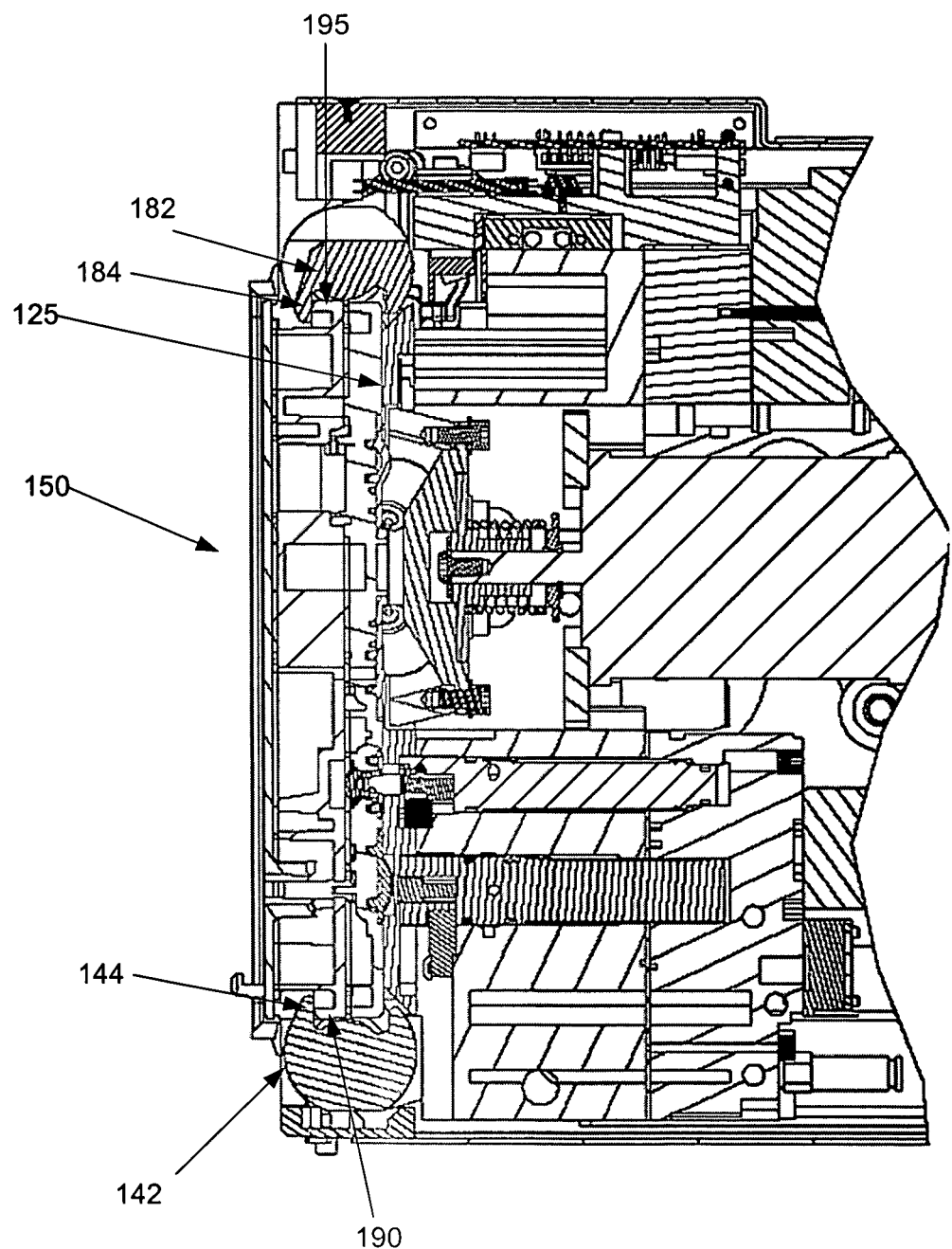
FIG. 5 is a diagrammatic representation illustrating a cross-sectional view of one embodiment of a cassette in a cassette receiver.

FIG. 5 is a cross-section of one embodiment of cassette 150 inserted into cassette receiver 125. Cassette 150 is held in place by a clamp. In the embodiment of FIG. 5, the clamp includes lower clamp rail 142 and upper clamp rail 182, though in other embodiments the clamp can contact cassette 150 in other areas. When cassette 150 is initially inserted, clamp rails 142/182 rotate so that clamping fingers (e.g., clamp finger 144 and clamp finger 184) contact cassette 150 in the clamping zones. For example, clamp finger 144 contacts cassette 150 at clamping portion 190 while clamp finger 184 can contact cassette 150 at clamping portion 195. Rotation can be imparted to the clamp rails 142/182 from the force of insertion, by a motor, by an air cylinder or by a combination of any of these. To release the cassette, the clamp rails 142/182 rotate in the opposite direction. When inserted, surgical console interface section 170 can contact surgical console 100 such that, for example, peristaltic pump rollers 140 can squeeze flow channel 177.

In the embodiment of FIG. 5, the clamp fingers push cassette 150 towards surgical console 100 to hold cassette 150 in place. During a procedure, peristaltic pump roller 140 will assert a force on cassette 150 (e.g., to squeeze flow channel 177) resulting in a greater force at the clamping portions 190 and 195. Because the face of a clamping portion that contacts the clamp may not be parallel with the clamp, the force applied by the clamp may not be evenly distributed. For example, if the rearward facing face of clamping portion 195 is not parallel with clamp finger 184, the force imparted by clamp finger 184 will not have a uniform force profile. According to embodiments of the present invention, clamping portion 195 can include a set of ribs to distribute the force as described below in conjunction with FIG. 7.

Figure 6:
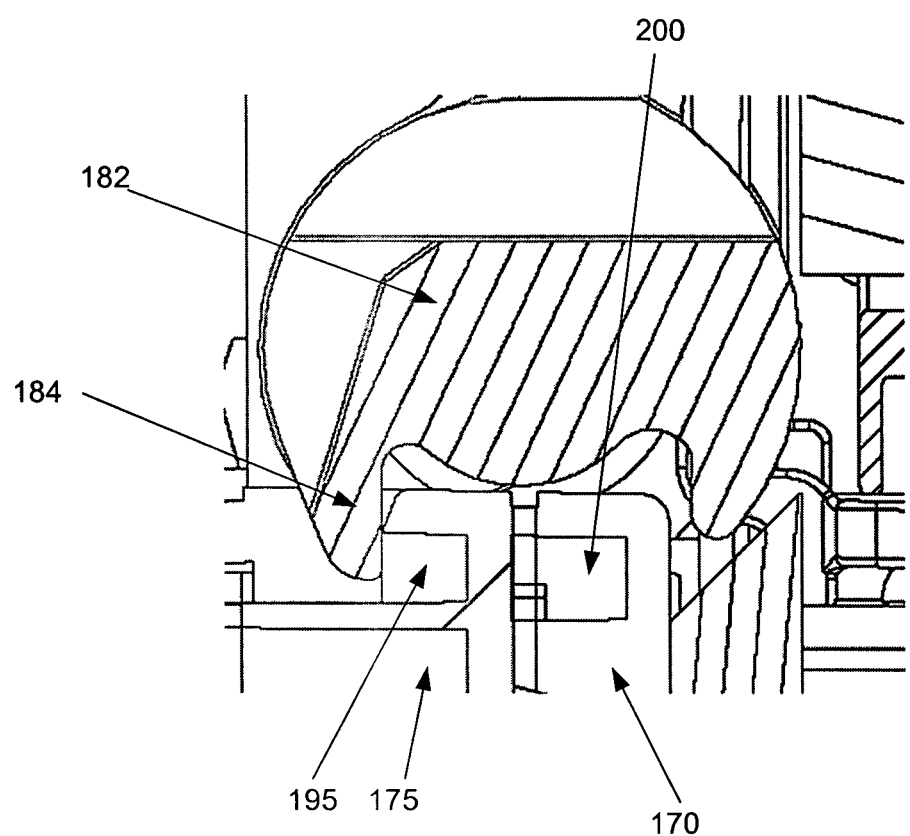
FIG. 6 is a detailed view of one embodiment of a cassette engaged with a clamp.
Figure 8:
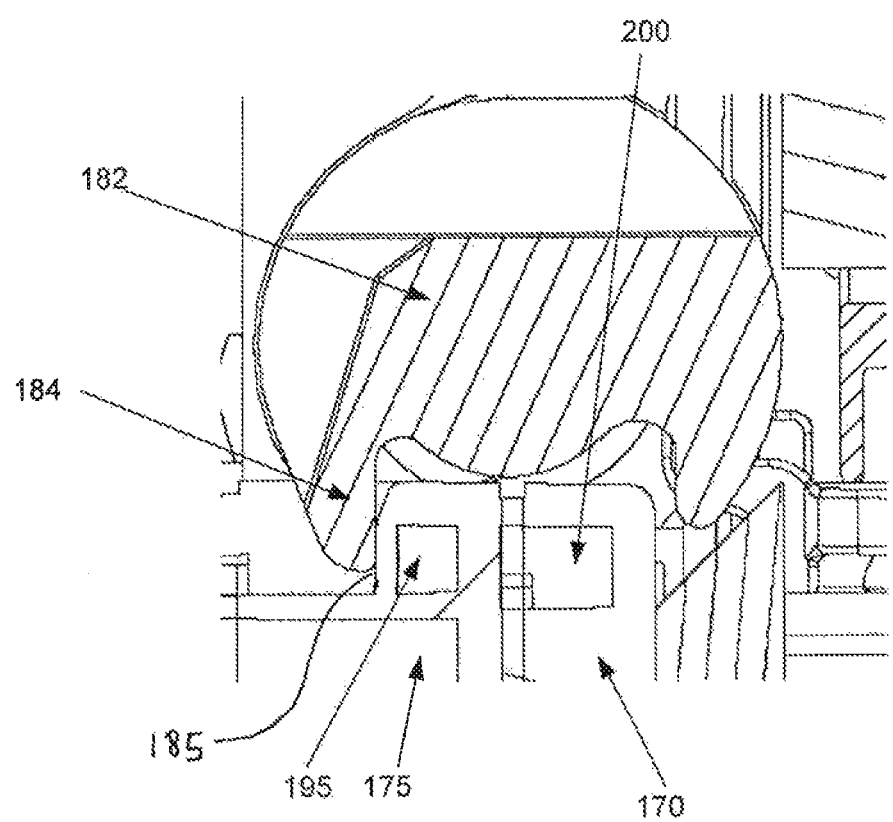
FIG. 8 is a detailed view of one embodiment of a cassette engaged with a clamp showing an interfacing wall in contact with the clamp.

FIG. 6 is a detail view of cassette 150 clamped by clamp rail 182. In the embodiment of FIG. 6, middle section 175 defines a portion of cassette body 155. Projecting from cassette body 155 (shown in FIG. 3) is clamping portion 195 to engage with clamp finger 184 of clamp rail 182. A set of ribs acts to distribute the force applied by clamp finger 184. In the embodiment of FIG. 6, the end faces of the ribs can contact the clamp. However, in other embodiments, the ribs can be disposed behind a surface that contacts the clamp (also referred to as an "interfacing wall"). FIG. 8 shows an example interfacing wall 185 that contacts the clamp. Additionally, console interface section 170 can include a clamping portion 200 projecting from the body portion of console interface section 170. Although the clamping portion 200 does not contact clamp finger 184, clamping portion 200 can also include a set of ribs to distribute the force applied to cassette 150.

Figure 7:
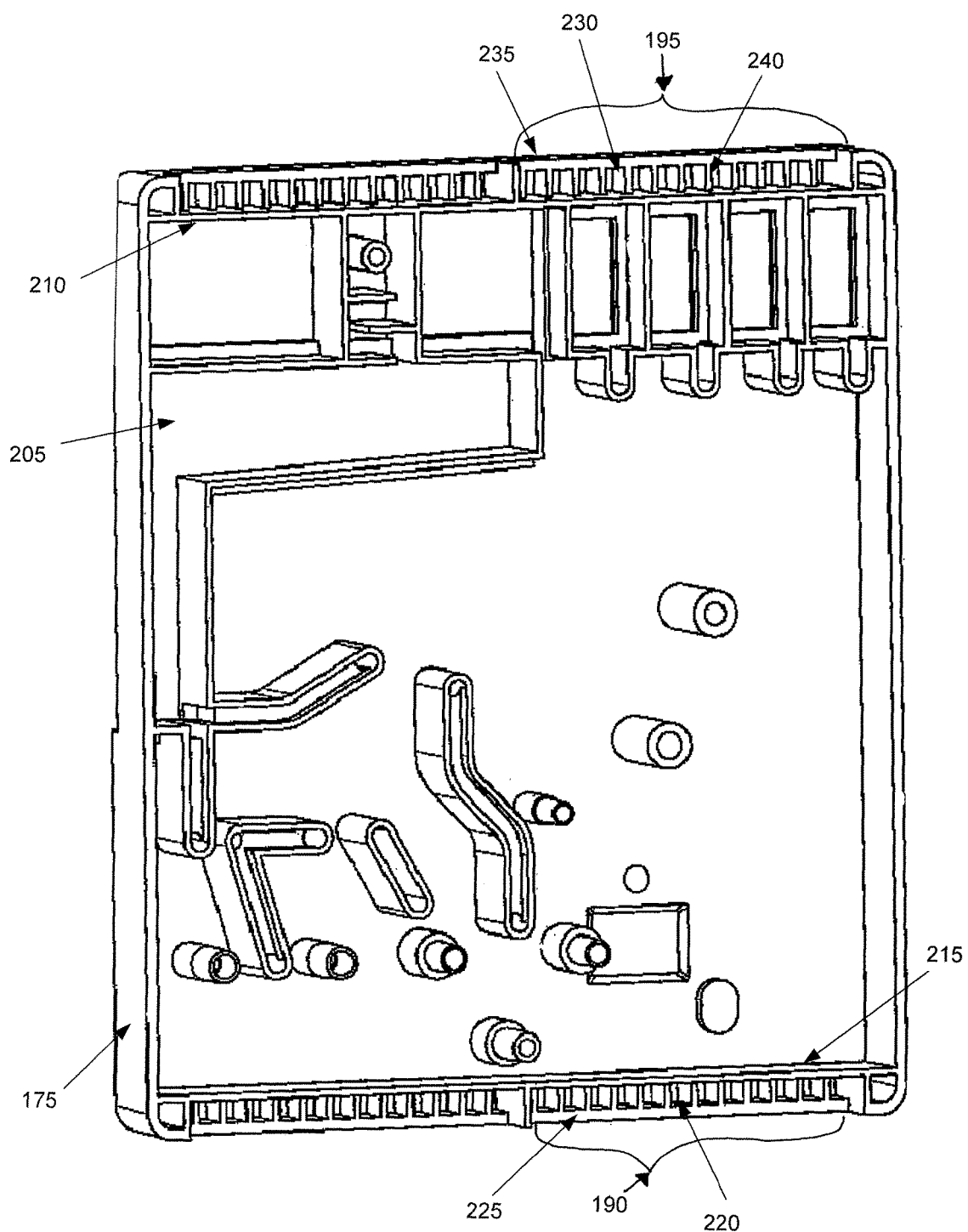
FIG. 7 is a diagrammatic representation of one embodiment of a cassette section including a clamping portion.

FIG. 7 is a diagrammatic representation of one embodiment of middle section 175 of cassette 150. Middle section 175 can include a body portion 205 to define a portion of cassette body 155 (shown in FIG. 3). Body portion 205 can include outer walls 210 and 215. In this example, body outer wall 210 is a top wall and body outer wall 215 is a bottom wall. Clamping portion 190 projects from body portion 205 and includes a set of ribs 220 transversely disposed between outer wall 215 and end wall 225. Similarly, clamping portion 195 projects from body portion 205 and includes a set of ribs 230 transversely disposed between outer wall 210 and end wall 235. The end faces of the ribs (e.g., end face 240) can contact the clamp (e.g., the clamping fingers) during use. According to other embodiments, the ribs can be behind a clamp interfacing wall configured to contact the clamp during use.

While FIG. 7 illustrates the ribs as evenly spaced ribs with generally rectangular cross sections, the ribs can be otherwise disposed and shaped. In general, the ribs can be formed of a material and shaped such that the ribs are stable when loaded. Each rib can be made of a plastic such that the rib will deform predictably in the elastic region and will flow plastically when the material yield point is reached. As a rib deforms in the elastic region, other ribs can engage the clamp (or deform further if already contacting the clamp) to distribute the load. Similarly, if a rib deforms plastically, adjacent ribs can engage the clamp (or deform further) to distribute the load. Embodiments of the present invention thus provide discrete small load areas that can deflect and distort predictably and non-cartographically at high loads. This allows for the absorption of accumulated tolerances while still providing a distributed load on the cassette as the cassette conforms to the load profile put on it.

Put another way, because the clamp and cassette may not be parallel due to machining and assembly tolerances, for example, the load profile imparted by the clamp may be non-uniform. The clamping portion of cassette 150 can conform to the load profile (e.g., by the ribs in the areas of higher loads deforming more) to distribute the load. Consequently, a non-uniformly distributed high load can be distributed in the clamping portion without causing catastrophic failure to cassette 150. The ribs can be sized and shaped depending on the expected load the cassette will experience.

While FIG. 7 illustrates one embodiment of middle section 175, similar clamping portions can also be included in console interface section 170 or otherwise included in cassette 150. Body portion 205, clamping portion 190 and clamping portion 195 can be a unitary piece of injection molded plastic, separate assemblies coupled together or otherwise attached.

Embodiments of the present invention provide a surgical cassette with clamping portions to interface with a clamp and distribute the load applied by the clamp. The clamping portion can comprise a set of ribs to distribute the load of the clamp. Each rib in the set of ribs can be formed of a material that deforms elastically in an elastic region and plastically when a material yield point is reached. Consequently, the clamping portion can, according to one embodiment, conform to the load profile put on it.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed in the following claims.

What is claimed is:

1. A surgical cassette configured to interface with a clamp of a surgical receiver of a surgical system comprising:
   a body portion comprising an outer wall on a first side of the surgical cassette; and
   a clamping portion projecting from the outer wall of the body portion and configured to contact clamp during use, the clamping portion comprising:
   an end wall forming an exterior surface of the surgical cassette; and
   a set of ribs transversely disposed between the outer wall of the body portion and the end wall of the clamping portion, the set of ribs configured to distribute a load asserted by the clamp on the surgical cassette and to deform elastically and/or plastically to conform to a load profile corresponding to the load asserted by the clamp on the surgical cassette.

2. The surgical cassette of claim 1, wherein each rib of the set of ribs comprises an end face and the clamping portion is configured to contact the clamp at one or more of the end faces.

3. The surgical cassette of claim 1, wherein the clamping portion and the body portion are formed from an integral piece of plastic.

4. The surgical cassette of claim 1, wherein the clamping portion is disposed on a first side of the surgical cassette.

5. The surgical cassette of claim 1, further comprising an additional outer wall on a second side of the body portion opposite the first side and an additional clamping portion projecting from the additional outer wall.

6. The surgical cassette of claim 1, wherein the body portion comprises:
a first body portion; and
a second body portion adjacent the first body portion; and
wherein the clamping portion comprises:
a first clamping portion projecting from the first body portion; and
a second clamping portion projecting from the second body portion.

7. The surgical cassette of claim 6, wherein the set of ribs comprises a first set of ribs formed in the first clamping portion and a second set of ribs formed in the second clamping portion.

8. The surgical cassette of claim 7, wherein the first clamping portion is adjacent to the second clamping portion such that the first set of ribs is adjacent to the second set of ribs.

9. The surgical cassette of claim 6, wherein the body portion further comprises a third body portion adjacent to the first body portion, wherein the first body portion, the third body portion, and the first clamping portion define a recess of the surgical cassette, and wherein a sidewall of the recess defines a clamping surface of the clamping portion.

10. The surgical cassette of claim 9, wherein the first body portion, the second body portion, and the third body portion are integrally formed.

11. The surgical cassette of claim 1, wherein end faces of the set of ribs define a clamping surface adapted to engage the clamp.

12. The surgical cassette of claim 1, wherein the clamping portion further comprises a clamp interfacing wall having a first surface adapted to contact the clamp and a second surface opposite the first surface, wherein the set of ribs are disposed adjacent to the second surface, and wherein the set of ribs are disposed transversely to the clamp interfacing wall.

13. The surgical cassette of claim 6, wherein the first clamping portion is distinct from the second clamping portion.

14. The surgical cassette of claim 1, wherein the body portion further comprises a fluid flow channel.

15. The surgical cassette of claim 1, wherein the body portion comprises a handle coupled to the body portion.

* * * * *